(12) United States Patent
Siefert

(10) Patent No.: US 8,523,839 B2
(45) Date of Patent: Sep. 3, 2013

(54) SYSTEM AND METHOD FOR PUMPING INTRAVENOUS FLUID

(75) Inventor: Robert Siefert, Escondido, CA (US)

(73) Assignee: CareFusion, Inc., San Diego, CA (US)

( * ) Notice: Subject to any disclaimer, the term of this patent is extended or adjusted under 35 U.S.C. 154(b) by 0 days.

(21) Appl. No.: 13/291,010

(22) Filed: Nov. 7, 2011

(65) Prior Publication Data
US 2012/0059350 A1    Mar. 8, 2012

Related U.S. Application Data

(63) Continuation of application No. 12/511,886, filed on Jul. 29, 2009, now Pat. No. 8,088,106.

(51) Int. Cl.
*A61M 31/00* (2006.01)
(52) U.S. Cl.
USPC ............................ 604/500; 604/152; 604/506
(58) Field of Classification Search
USPC .................. 604/29, 30, 151, 152, 890.1, 500, 604/506; 417/16, 395
See application file for complete search history.

(56) References Cited

U.S. PATENT DOCUMENTS

| | | | |
|---|---|---|---|
| 5,378,126 A | 1/1995 | Abrahamson et al. | |
| 5,989,423 A | 11/1999 | Kamen et al. | |
| 8,088,106 B2 * | 1/2012 | Siefert | 604/152 |
| 2003/0217962 A1 * | 11/2003 | Childers et al. | 210/258 |
| 2009/0035152 A1 * | 2/2009 | Butterfield | 417/53 |

FOREIGN PATENT DOCUMENTS

WO    2009017487    2/2009

OTHER PUBLICATIONS

International Preliminary Report on Patentability for PCT/US2010/043588 mailed Oct. 3, 2011.
Amendment Under Article 34 PCT for PCT/US2010/043588 dated Mar. 2, 2011.

* cited by examiner

*Primary Examiner* — Theodore Stigell
(74) *Attorney, Agent, or Firm* — McDermott Will & Emery LLP

(57) ABSTRACT

An intravenous fluid pump (IV) contains a disposable part including a fluid chamber having a resilient top membrane and a non-disposable part including a piston abutting a resilient membrane and a vacuum chamber fitted on top of the resilient top membrane. An external pump is used to create vacuum in the vacuum chamber, resulting in the resilient top membrane being held taut. The flow rate through the pump is relatively independent of changes in the pressure of IV fluid on the upstream and the downstream due to changes in the relative elevation of the fluid reservoir and the patient with respect to the fluid pump.

9 Claims, 6 Drawing Sheets

SYSTEM AND METHOD FOR PUMPING INTRAVENOUS FLUID

This application is a continuation of U.S. application Ser. No. 12/511,886, filed on Jul. 29, 2009 and issued as U.S. Pat. No. 8,088,106, which is hereby incorporated by reference in its entirety.

FIELD

The present invention relates, in general, to fluid delivery systems and, more particularly, to a method of maintaining flow rate accuracy in an intravenous fluid delivery system.

BACKGROUND

Intravenous (IV) fluid delivery pumps are used to deliver fluid to a patient or to draw out fluid from a patient's body. The delivery of fluid is achieved by using gravity and/or a pump. A typical pump-based IV fluid delivery system includes a pump connected to a fluid reservoir via an inlet tube and to a patent via an outlet tube. During normal fluid delivery operation, the pump moves fluid from the reservoir to the patient at a certain flow rate. The flow rate may be controlled by a medical professional. Certain applications require that the fluid delivery system strictly adhere to the flow rate set by a medical professional.

The actual flow rate of delivery for certain IV fluid pumps presently available in the market is sensitive to variations in upstream and downstream fluid pressures. Such variations occur when the relative elevation of the pump with respect to a reservoir or a patient is changed. Furthermore, small bore IV tubing and filters on the output can result in high output pressures. Certain fluid delivery pumps, e.g., as disclosed in the U. S. Patent Application No. 2009/0035152, use the resiliency property of a membrane in fluid contact with the fluid being delivered to control the rate of flow. In such fluid delivery pumps, negative upstream (inlet tube) or downstream (outlet tube) pressures can cause partial or complete collapse of the flexible membrane of a disposable fluid chamber used with the pumping mechanism. To mitigate the problem, the affected membrane sections of the disposable fluid chamber have traditionally been made from springy, resilient material, such as silicone so that the section can self-inflate against a negative (opposing) pressure. Other methods may include attaching a piston or a pump to the disposable fluid chamber using magnets or other physical devices so that the pump can pull on the chamber as well as push to perform the pumping action. Such methods can often adversely affect the flow rate accuracy, since transitions from pushing to pulling can be difficult to accomplish in a uniform and continuous fashion.

SUMMARY

There is a need for a fluid delivery system that exhibits relatively constant flow rate of delivery, regardless of the upstream and downstream fluid pressures.

This and other needs are met by embodiments consistent with the present disclosure that provide a fluid pump design in which a vacuum chamber is positioned adjacent to the fluid chamber.

The earlier stated need and others are also met by embodiments of the present invention which provide an opening in the vacuum chamber from which air can be removed to create at least a partial vacuum in the vacuum chamber.

The earlier stated need and others are also met by still other embodiments of the present invention which provide a method of pumping fluid pushing against a resilient membrane of a fluid reservoir using a piston. The vacuum chamber holds the resilient membrane taut against the piston and ensures that the resilient membrane stays taut regardless of the fluid pressure in the fluid chamber.

In one exemplary aspect, a system for delivery of intravenous fluid is disclosed, comprising a disposable portion in contact with the intravenous fluid during delivery of the intravenous fluid, and a non-disposable portion isolated from contact with the intravenous fluid during delivery of the intravenous fluid, wherein the disposable portion comprises a fluid chamber having an opening and a pumping membrane positioned to form a side of the fluid chamber, and the non-disposable portion comprises a vacuum chamber positioned adjacent to the pumping membrane, the vacuum chamber configured to hold vacuum during delivery of the intravenous fluid.

In a second exemplary aspect, a method of delivering fluid from a reservoir to a patient-side instrument, the method comprising providing a fluid chamber with a pumping side, the fluid chamber having an opening for allowing fluid in and out of the fluid chamber, providing a vacuum chamber; the vacuum chamber sharing the pumping side with the fluid chamber and further having a sealing side, providing a piston touching the pumping side, removing at least some air from the vacuum chamber so that the pressure in the vacuum chamber is less than the pressure in the fluid chamber, and pumping fluid through the fluid chamber by alternating between moving the piston outwards to allow fluid to enter the fluid chamber and pushing the piston inwards to expel fluid from the fluid chamber is disclosed.

In a third exemplary aspect, a fluid delivery apparatus is disclosed comprising a fluid chamber, an inlet valve controllably coupling the fluid chamber to an inlet tube, an outlet valve controllably coupling the fluid chamber to an outlet tube, a pumping membrane defining at least one portion of the fluid chamber, a sealing membrane positioned to form a vacuum chamber between the pumping membrane and the sealing membrane, and a piston positioned against the pumping membrane and coupled to the sealing membrane and configured to reciprocate against the pumping membrane to reduce and expand the fluid chamber and thereby pump fluid in and out of the fluid chamber, the sealing membrane moving with the piston and maintaining a reduced pressure in the vacuum chamber.

The foregoing and other features, aspects and advantages of the embodiments of the present invention will become more apparent from the following detailed description and accompanying drawings.

DETAILED DESCRIPTION

The embodiments of the present disclosure address and solve problems related to the inaccurate flow rates due to elevation changes with respect to a fluid pump, of a fluid reservoir or a patient. In particular, the embodiments of the present disclosure provide a vacuum chamber adjacent to a fluid chamber to maintain a negative pressure differential between the pressure in the vacuum chamber and the pressure in the fluid chamber. The fluid in the fluid chamber is pumped via a pumping mechanism such as a piston or a pressure balloon. For example, when using a piston mechanism, the vacuum chamber may be disposed adjacent to the fluid chamber to maintain vacuum and the piston head may be disposed to push against a side of the fluid chamber. Embodiments of the disclosure achieve this, at least in part, by providing a resealable valve to the vacuum chamber. Using the valve, an external pump can be employed to remove air from the vacuum chamber. Upon removal of air, the resealable valve is closed airtight. Sufficient air is removed from the vacuum chamber so that regardless of the elevation of the reservoir or the patient-side instrument, the pressure in the inlet and the outlet tubes will always be higher compared to the pressure in the vacuum chamber. Since no relative negative pressure in the IV fluid is encountered, the pump fluid chamber will not collapse and fluid delivery will occur with high flow rate accuracy.

Figure 1:
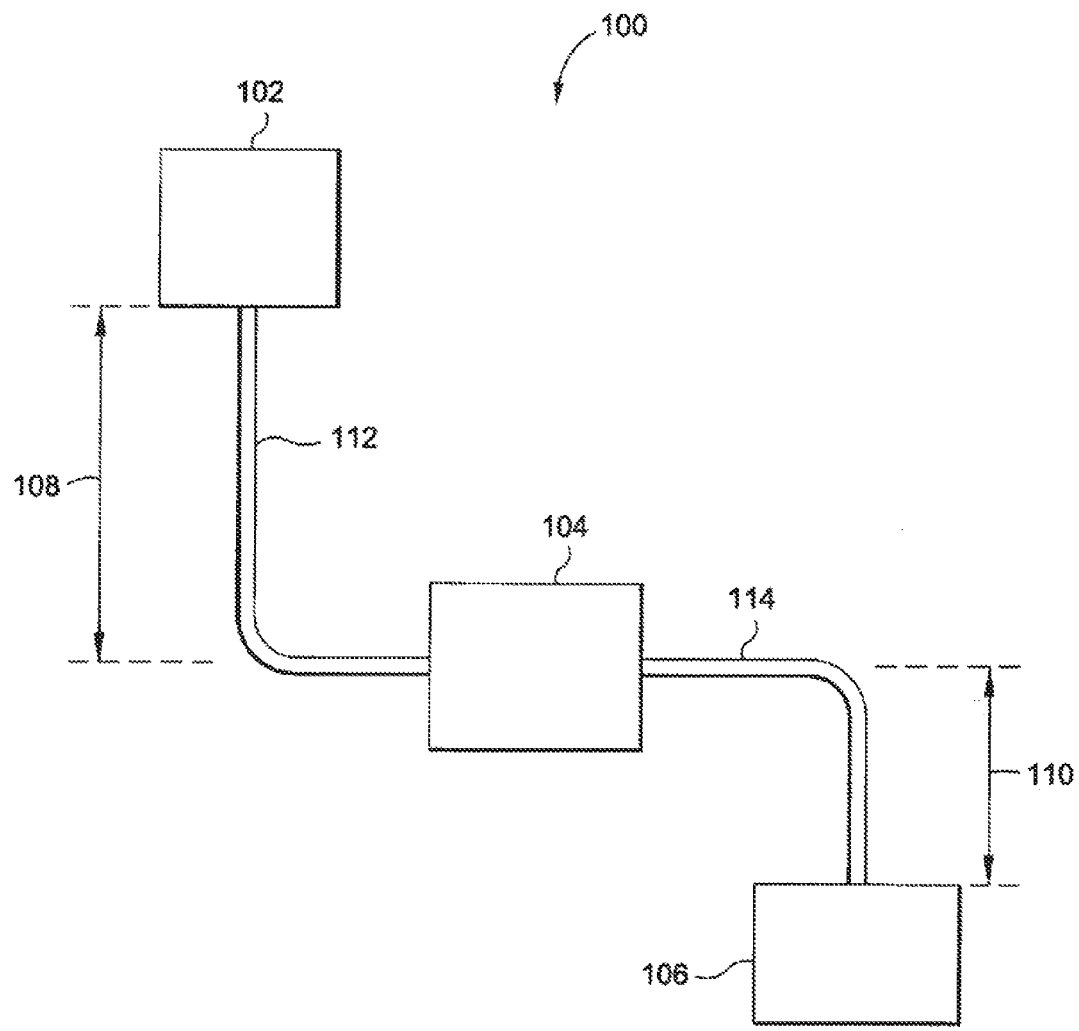
FIG. 1 is a block diagram depicting a fluid delivery system for use with embodiments of the present disclosure.

FIG. 1 shows a fluid delivery system 100 generally useful with embodiments of the present disclosure. A fluid reservoir 102 is connected to a fluid pump 104 via a fluid inlet tube 112. The fluid pump 104 is in turn connected to a patient or a patient-side instrument 106 via a fluid outlet tube 114. It is typical to hold the fluid reservoir 102 at a higher elevation with respect to the patient 106, with the fluid pump 104 positioned vertically between the reservoir 102 and the patient 106. Therefore, the elevation difference 108 between the reservoir 102 and the fluid pump 104 is typically positive, thereby resulting in the upstream fluid pressure in the inlet tube 112 being higher than ambient (atmospheric) pressure. Similarly, the elevation difference 110 of the fluid pump 104 with respect to the patient 106 is typically higher. Therefore, fluid in the outlet tube 114 will be typically at a fluid pressure lower than the ambient pressure. Because the patient, in the illustrated configuration, is at a lower elevation than the fluid pump 104, the fluid pump 104 has to hold back fluid in the fluid pump 104 to ensure that fluid does not flow down (siphon) to the patient before the fluid pump 104 expels the fluid in a controlled manner.

In certain situations during administration of IV fluids, e.g., when a patient is being transported, the positive elevation differences 108 and 110 may not be maintained by the medical staff. The elevation differences 108 and 110 may either become negative or may keep changing over time due to mobility of the patient and the fluid delivery system. As described in greater details below, the fluid pump embodiments of the present disclosure maintain flow rate accuracy under a wide range of values of the elevation differences 108 and 110.

Figure 2:
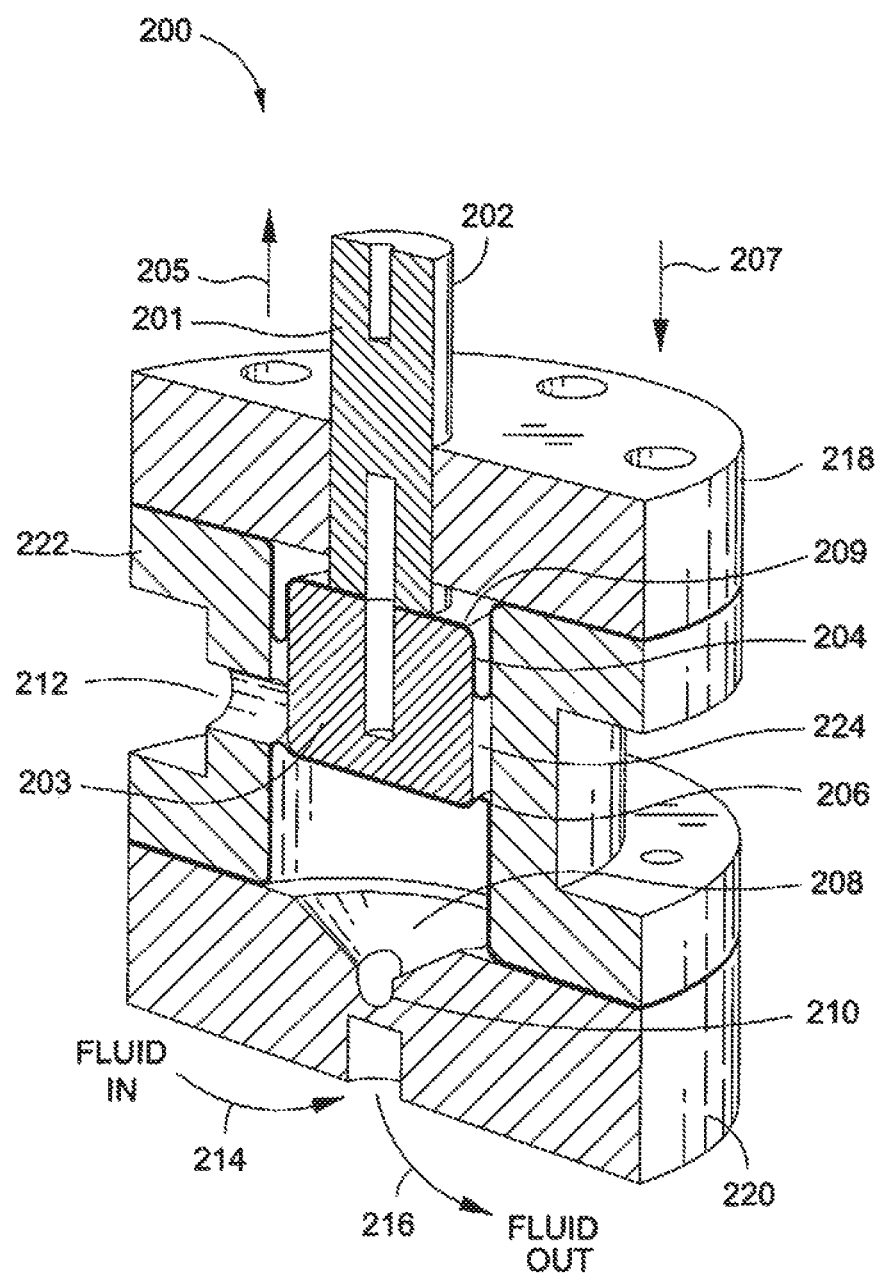
FIG. 2 is a cross-sectional perspective view of a chamber-and-pump assembly of a fluid pump apparatus in accordance with embodiments of the present disclosure.

FIG. 2 is a cross-sectional view of a chamber-and-pump assembly of an embodiment of a fluid pump 200 in accordance with the present disclosure. The cut away view is through the center line of the assembly, from an elevation slightly above, looking downward. A piston assembly 202, having a piston shaft 201 and a piston head 203, is fitted in a upper casing 218 of the fluid pump 200 such that the piston head 203 is able to push against the pumping membrane 206 of a fluid chamber 208. On a side of the fluid chamber 208 away from the piston assembly 202, an opening 210 is provided in the lower casing 220 such that fluid can enter in the fluid chamber 208 (arrow 214) when the piston head 203 is being pulled outwardly in the direction of arrow 205, and be expelled out (arrow 216) of the fluid chamber 208 when the piston head 203 is being pushed inwardly in the direction of arrow 207. A sealing membrane 204 is provided at the top end 209 of the piston head 203 to form an airtight connection with the piston head 203. The piston head 203 extends through the sealing membrane 204 and presses against the pumping membrane 206 having sufficient flexibility to move back and forth with the piston's movement. A vacuum chamber 224 formed between the sealing membrane 204 and the pumping membrane 206 is enclosed by a casing 222. In certain embodiments, the casing 222 is made of hard, non-resilient material such as plastic. The casing 222 is designed to make the vacuum chamber 224 airtight, except for an opening 212 for removing air out of the chamber 224 using an external suction pump (not shown in the figure). After removing the air, the opening 212 can be sealed by a user to make the vacuum chamber 224 airtight.

In certain configuration, the pumping membrane 206 may be made of a flexible but not stretchable material. A high tensile strength and relatively inelastic polyurethane membrane is advantageous in maintaining volume of the fluid chamber by withstanding pressure changes over a wide range, thereby maintaining flow rate accuracy over a range of fluid pressure values. In certain configurations, the pumping membrane 206 may be extended in the area between the vacuum chamber casing 222 and the lower casing 220 and may be advantageously exposed to allow measurement of pressure in the fluid chamber by an external probe (not shown in the figure).

Figure 3:
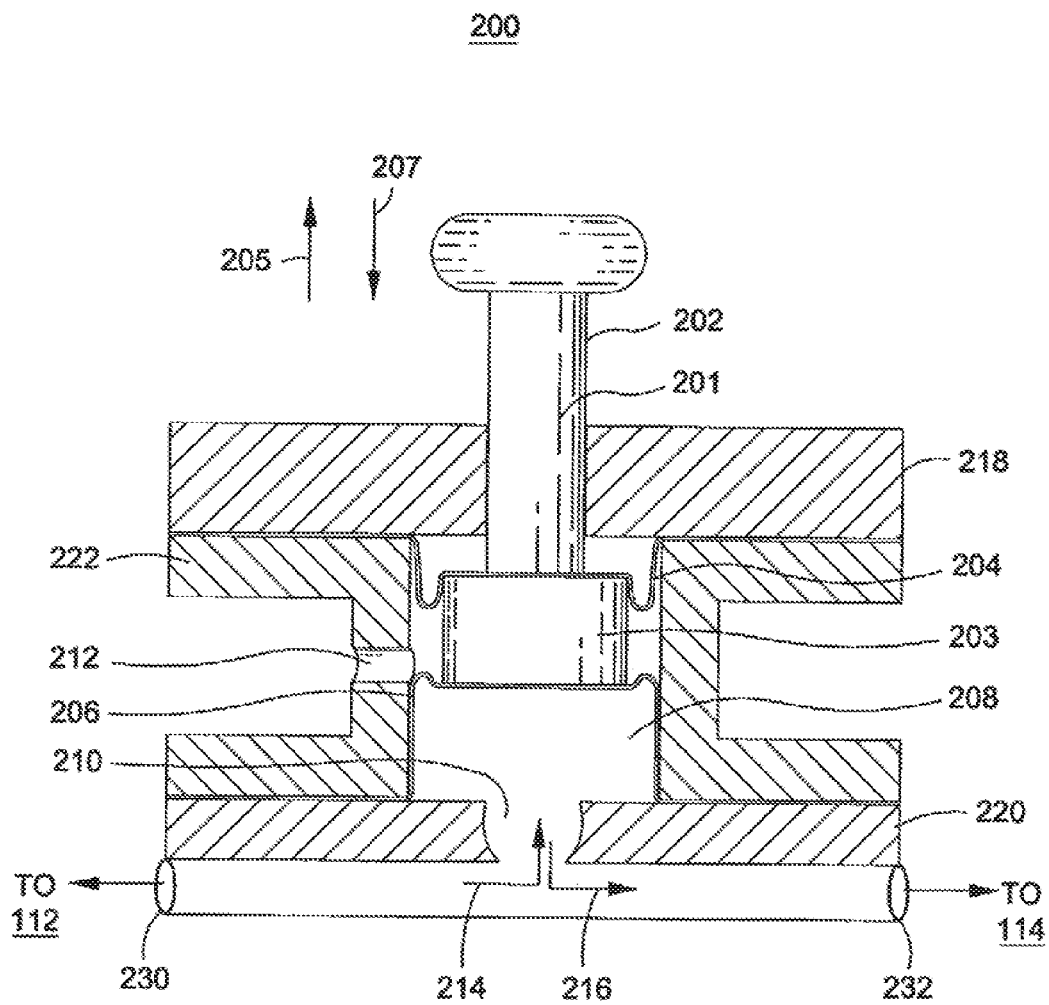
FIG. 3 is a cross-sectional view of the chamber-and-pump assembly of FIG. 2, with the piston pulled outwards, in accordance with embodiments of the present disclosure.

FIG. 3 shows a cross-sectional view of the fluid pump 200 with the piston head 203 pulled outwards to the top of its stroke. With the piston head 203 pulled out, the volume of the fluid chamber 208 is at its maximum. An external electromechanical mechanism (not shown in the figure) opens the input valve 230 disposed on the reservoir side to be open, allowing passage of fluid. The external electromechanical mechanism closes the output valve 232 disposed on the patient side, thereby disallowing passage of fluid into the outlet tube 114. With the input valve 230 open, fluid is allowed to flow in from the reservoir (arrow 214). The sealing membrane 204 is pulled back with the piston head 203, with the vacuum chamber 224 separating the sealing membrane 204 and the pumping membrane 206. As discussed above, the opening 212 is sealed airtight during the pumping operation of the fluid pump 200, thereby maintaining vacuum in the vacuum chamber 224. Because of the vacuum in the chamber 224, pressure on the fluid side of the pumping membrane 206 will be higher than the other side of the pumping membrane 206 (the vacuum chamber side). Therefore, regardless of the difference between the fluid pressure in the inlet tube 112 and the ambient pressure (a function of the elevation 108 of the reservoir 102), the presence of vacuum in the vacuum chamber 224 will ensure that substantially the same amount of fluid is drawn into the fluid chamber 208 as the piston head 203 is moved to the top of its stroke. The volume of fluid drawn in each stroke will be equal to the displacement capacity of the piston assembly 202, regardless of the elevation of the reservoir 102.

Figure 4:
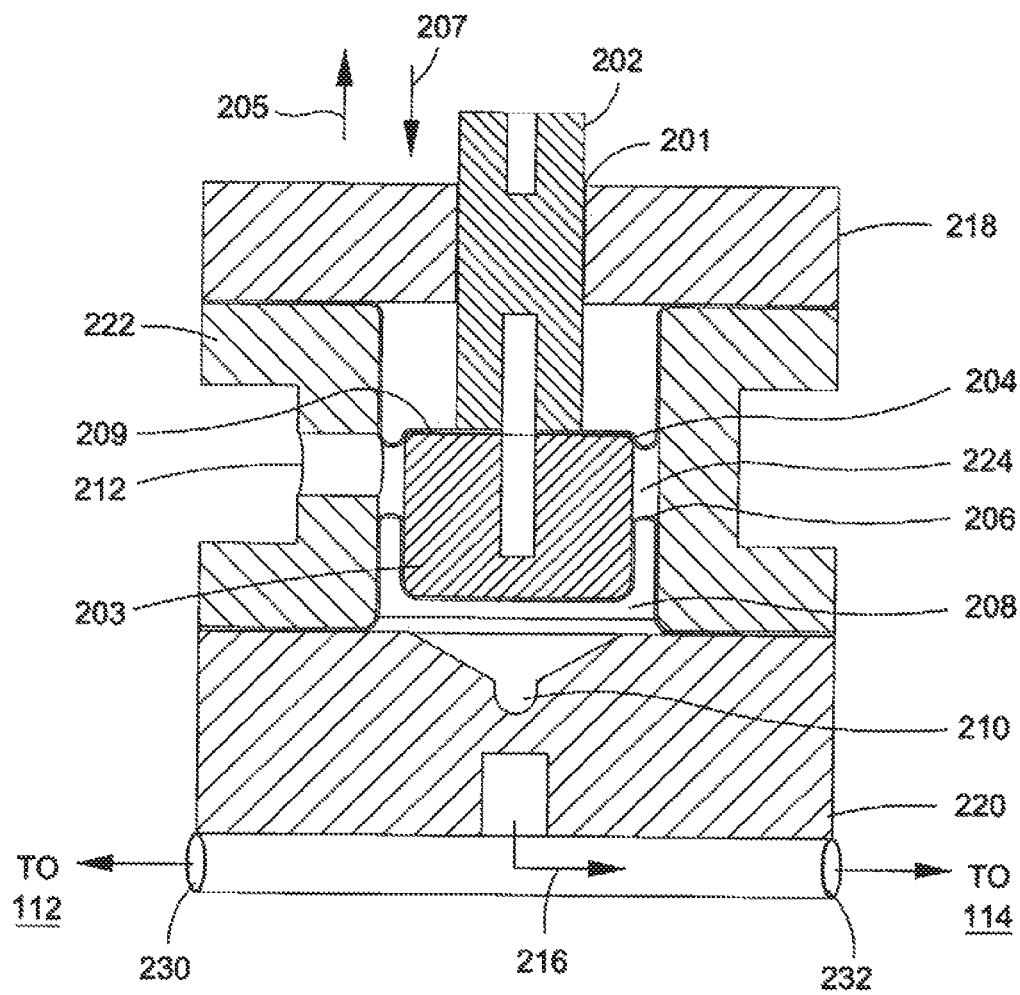
FIG. 4 is a sectional view of the chamber-and-pump assembly of FIG. 2, with the piston pushed inwards, in accordance with embodiments of the present disclosure.

FIG. 4 shows a cross-sectional view of the fluid pump assembly 200 with the piston head 203 at the bottom of its stroke. When the piston head 203 is at the bottom of its stroke, the sealing membrane 204 may be stretched towards the fluid chamber 208. The pumping membrane 206 is pushed downwards by the piston head 203, thereby resulting in reduction in the volume of the fluid chamber 208. An external electromechanical mechanism closes the input valve 230 and opens the output valve 232. The fluid contained in the fluid chamber 208 is expelled out of the opening 210 towards the patient (arrow 216). The output valve 232 operates to allow fluid to flow out of the fluid chamber 208 and the input valve 230 operates to stop fluid from the inlet tube 112 to flow into the chamber 208. Because vacuum opening 212 is sealed during the pumping operation, the chamber 224 still contains vacuum. Due to vacuum in chamber 224 on the outside of the pumping membrane 206, the pressure difference between fluid in fluid chamber 208 and the vacuum chamber will be positive. As a result, the amount of fluid expelled out of the fluid chamber 208 by the downward movement of the piston head 203 will be substantially independent of the elevation difference between the fluid pump 200 and the patient 106. The amount of fluid expelled into the outlet tube 114 in one stroke will be equal to the displacement capacity of the piston assembly 202.

The valves 230 and 232 are designed to facilitate unidirectional flow of fluid through the opening 210. For example, in certain embodiments, the valves 230, 232 may be configured to operate in two positions that include an inflow position, and an outflow position. In certain embodiments, the valves 230, 232 may also operationally include a closed position. in which the valves 230, 232 do not allow flow of fluid either in or out of the inlet tube 112 and the outlet tube 114 respectively. When the piston head 203 begins to move outwards, creating suction pressure on the fluid chamber 208, the input valve 230 may move into the inflow position in which the input valve 230 allows fluid from the inlet tube 112 to flow into the fluid chamber 208, The output valve 232 may also move into its inflow position in which the output valve 232 prevents fluid from flowing out of the fluid chamber 208 into the outlet tube 114. When the piston head 203 is moving inwards, creating ejection pressure on the fluid chamber 208, the output valve 232 may move into the outflow position in which it allows fluid from the fluid chamber 208 to expel out into the outlet tube 114. In the outflow position, input valve 230 prevents fluid from the inlet tube 112 from entering the fluid chamber 208.

In certain embodiments, removal of air from the vacuum chamber 224 results in only partial vacuum (not total vacuum) in the vacuum chamber 224. As noted above, a relatively constant flow rate can be maintained as long as the pressure difference between fluid in the fluid chamber 208 and the vacuum chamber 224 is positive. Therefore, in certain embodiments, a user may remove just enough air from the vacuum chamber 224 to ensure such a pressure differential exists, based on the expected operational values for the elevation differences 108 and 110.

Figure 5:
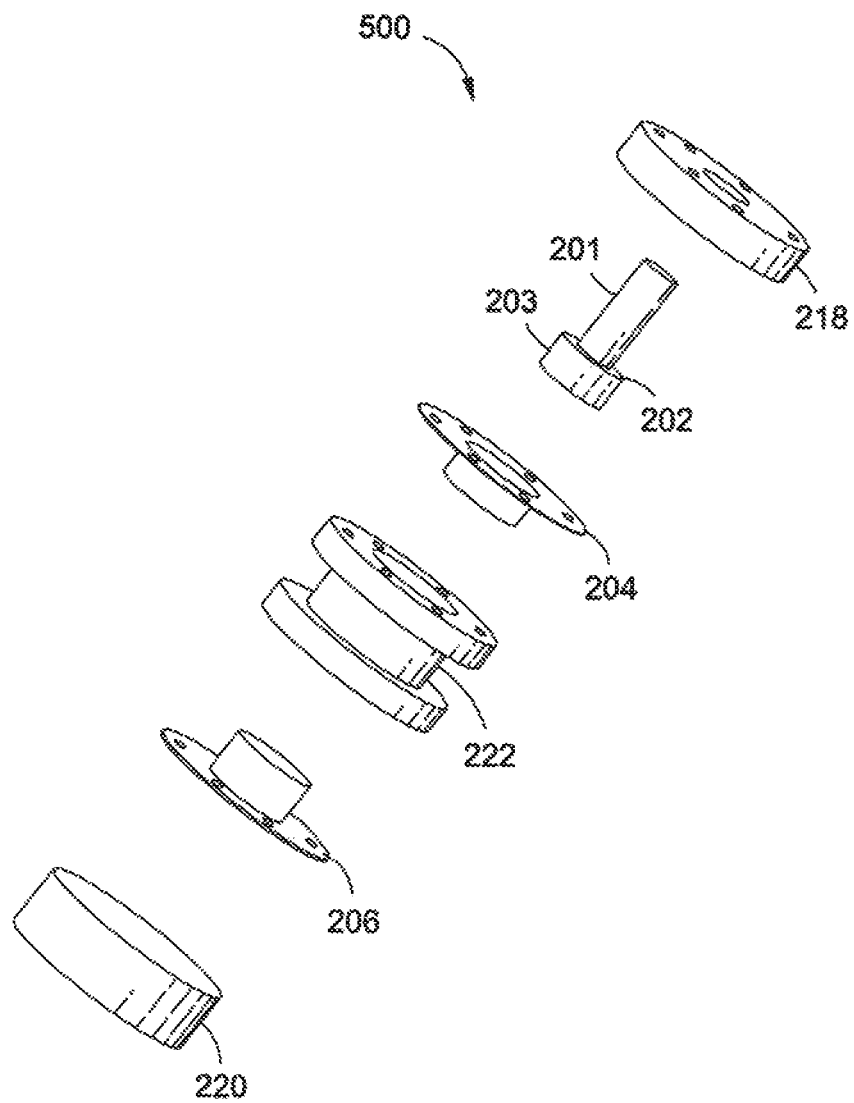
FIG. 5 is an exploded view of components of a chamber-and-pump assembly of a fluid pump apparatus assembly, in accordance with embodiments of the present disclosure.

FIG. 5 is an exploded view of various components of the fluid pump 200, in accordance with certain embodiments of the present disclosure. The vacuum chamber 222 is hollow and is provided with the opening 212 (not shown in the figure). On its top side, casing of the vacuum chamber 224 is fitted with the resilient membrane 204. The piston assembly 202 is positioned such that the piston shaft 201 passes through the sealing membrane 204 and piston head 203 is able to push against the pumping membrane 206. The top assembly is held in position by the casing 218. On the bottom side, the vacuum chamber casing 222 is fitted with the pumping membrane 206, held in place by the fitting 220. Fasteners needed to assemble these various components are omitted from the figure.

In certain embodiments of the fluid delivery system consistent with the present disclosure, the fluid delivery system comprises a disposable part and a non-disposable part. For the safety of a patient and a medical practitioner using a fluid delivery system, all parts of the fluid delivery system that come in contact with the fluid during the use of the fluid delivery system may be disposed after a single use. Referring to FIGS. 1 through 5, the disposable parts may include the fitting 220, the pumping membrane 206, the opening 210 and the valves 230, 232. Because these parts are disposable, in certain embodiments, these parts may be made of relatively less durable material.

The non-disposable parts of a fluid delivery assembly embodiment consistent with the present disclosure may include parts that do not come in contact with fluid, and may include the vacuum chamber casing 222, the sealing membrane 204, the piston assembly 201 and the top assembly casing 218. It should be noted that while the sealing membrane 204 and the pumping membrane 206 are fitted to form sides of the vacuum chamber 224, the membranes 204 and 206 are not in fluid contact with each other. The non-disposable parts 222, 204, 201 and 218 will be used for multiple fluid deliveries. Therefore, in certain embodiments, these parts may be manufactured to last longer and with greater precision or more durable material. This advantageously helps with maintaining high flow rate accuracy by reducing wear related errors such as changes in the displacement capacity of the piston assembly 201 or airtightness of the vacuum chamber 224.

In certain embodiments, the disposable and the non-disposable components of a fluid pump may be attachable to each other using fastening mechanisms that result in a substantially airtight connection. This may be accomplished using well-known techniques including, but not limited to, the use of seal rings and fasteners or screw-thread-and-nut design in which one component is screwed to another (e.g., component 206 into component 202) to make an airtight connection.

Figure 6:
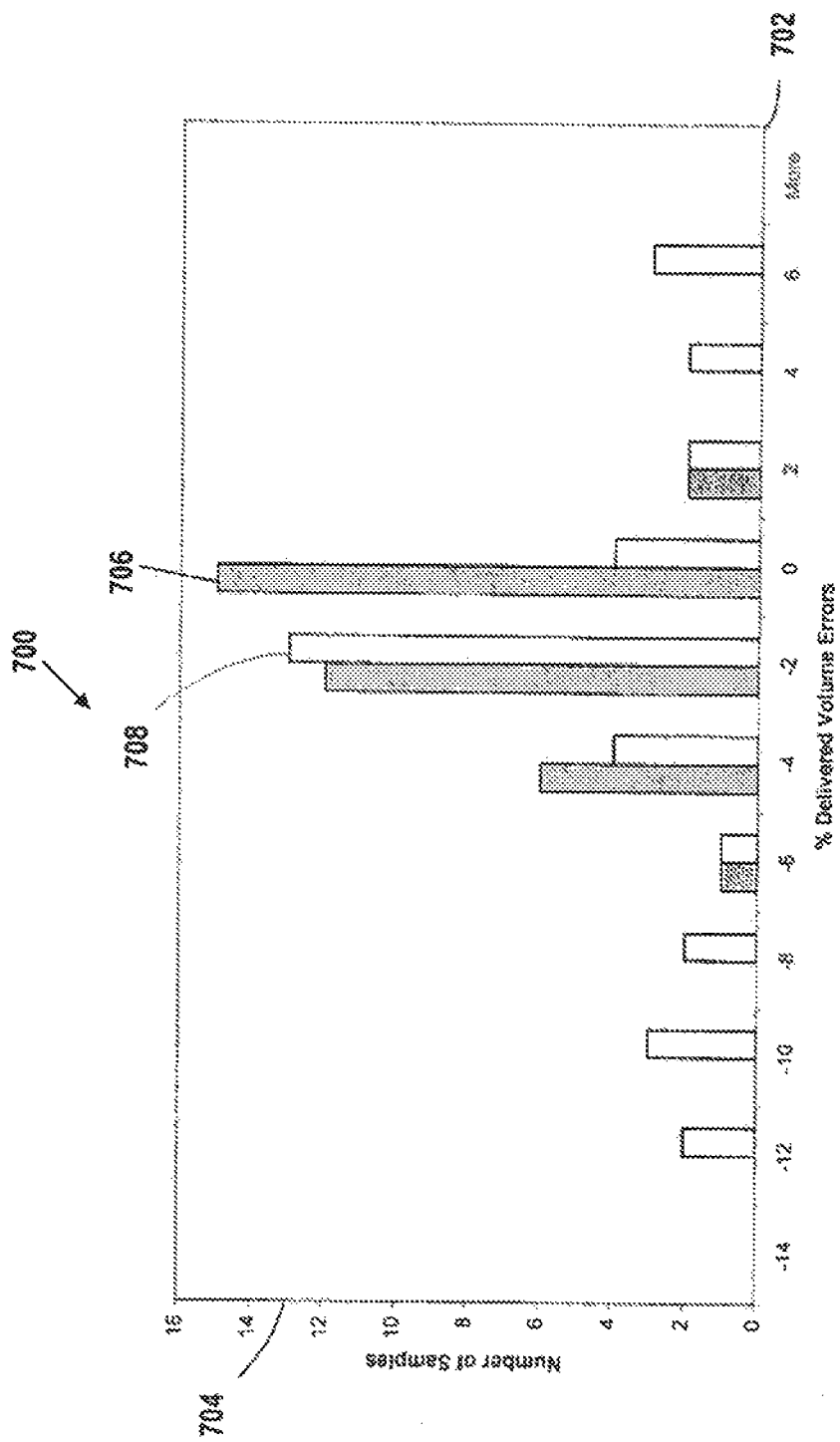
FIG. 6 is a histogram illustrating improvement in flow rate accuracy using a fluid pump apparatus in accordance with embodiments of the present disclosure.

FIG. 6 is a histogram 700 showing improvement in flow rate accuracy based on measurements performed using a prototype fluid pump embodiment consistent with the present disclosure. Two sets of measurements were made for flow rate accuracy, one set using an off-the-shelf "push membrane" type fluid pump, and the other set using the prototype embodiment. A total of thirty six measurements were made for flow rate from each pump by varying the pressure on the upstream side between −0.7 psi to +1 psi and the pressure on the downstream side between −2 psi to +6 psi. The variation in pressure was achieved by changing relative elevations of the reservoir and a simulated patient with respect to the fluid pump. The X axis 702 represents the percent difference from the intended (or nominal) flow rate. The Y axis 704 represents the number of actual flow rate measurements at a given percent difference from the nominal rate. The gray bars (e.g., 706) represent measurements for the prototype. The unshaded bars (e.g., 708) represent measurements for the off-the-shelf pump. The most frequently occurring measurement for the prototype was around zero percent variation from the average. All measurements for the prototype were between approximately −6% to 1% of the average. In contrast, the most common measurement for the off-the-shelf pump was −2%, with flow rate errors between approximately −13% to +6% of the average flow rate. These results may be interpreted to mean that when fluid pressure on the inlet or outlet side is varying in a fluid delivery system, the variations in the flow rate for the off-the-shelf pump tested is about 20%, while the variation in flow rate for the prototype is only about 7%. These results may be interpreted to mean that the maximum-to-minimum flow rate variation of the prototype is about one-third of the maximum-to-minimum flow rate variation of the off-the-shelf fluid pump, when measured over a number of possible pressure variations on both inlet and outlet sides.

The results presented in FIG. 6 highlight the flow rate advantage of a pump designed in accordance with the present disclosure. One of skill in the art will appreciate that removing air from the vacuum chamber results in inflation of the membrane on the disposable side of the pump. This vacuum creates a pressure that will generally be less than any foreseeable upstream or downstream pressures encountered by the IV fluid. Therefore, relative to the vacuum chamber, all IV pressures would appear to be positive, and at varying levels. Since the fluid pressure on the fluid side of the resilient membrane of the fluid chamber will always be greater than the non-fluid side of the resilient membrane, the resilient membrane of the fluid chamber will not collapse and a higher level of flow rate accuracy can be maintained.

Although embodiments of the present disclosure have been described and illustrated in detail, it is to be clearly understood that the same is by way of illustration and example only and is not to be taken by way of limitation, the scope of the present disclosure being limited only by the terms of the appended claims.

What is claimed is:

1. A method of delivering fluid from a reservoir to a patient-side instrument, the method comprising the steps of:
   providing a fluid chamber with a pumping membrane that is flexible but not stretchable, the fluid chamber having an opening for allowing fluid in and out of the fluid chamber;
   providing a vacuum chamber formed between the pumping membrane of the fluid chamber and a sealing membrane;
   providing a piston touching the pumping membrane;
   removing at least some air from the vacuum chamber so that the pressure in the vacuum chamber is less than the pressure in the fluid chamber; and
   pumping fluid through the fluid chamber by alternating between:
   moving the piston outwards to allow fluid to enter the fluid chamber without stretching the pumping membrane; and
   pushing the piston inwards to expel fluid from the fluid chamber without stretching the pumping membrane.

2. The method of claim 1, wherein said removing comprises reducing pressure in the vacuum chamber to a value responsive to an expected elevation difference between the fluid chamber and the reservoir.

3. The method of claim 1, wherein said removing comprises creating vacuum in the vacuum chamber.

4. The method of claim 1, wherein said removing comprises reducing pressure in the vacuum chamber to a value responsive to an expected elevation difference between the fluid chamber and the patient-side instrument.

5. The method of claim 1, further comprising:
   providing an inlet valve configured to allow passage of fluid from the reservoir to the fluid chamber when the piston is moving outwards; and
   providing an outlet valve configured to allow passage of fluid from the fluid chamber to the patient-side instrument when the piston is moving inwards.

6. A method of delivering intravenous fluid, the method comprising the steps of:
   removing air through an opening from a vacuum chamber that is formed between a pumping membrane that is flexible but not stretchable and forms a side of a fluid chamber of a disposable delivery element and a sealing membrane that is part of a non-disposable casing that is configured to form a seal with the pumping membrane;
   displacing the pumping membrane so as to decrease a volume of the fluid chamber without stretching the pumping membrane; and
   displacing the pumping membrane so as to increase the volume of the fluid chamber without stretching the pumping membrane.

7. The method of claim 6, further comprising the step of: sealing the opening.

8. The method of claim 6, wherein the step of displacing the pumping membrane so as to decrease a volume of the fluid chamber comprises moving a piston that is disposed within the vacuum chamber toward the fluid chamber.

9. The method of claim 6, wherein the step of displacing the pumping membrane so as to increase a volume of the fluid chamber comprises moving a piston that is disposed within the vacuum chamber away from the fluid chamber.

* * * * *